(12) United States Patent
Ries et al.

(10) Patent No.: US 7,537,493 B2
(45) Date of Patent: May 26, 2009

(54) METHOD FOR FORMING A CONNECTOR ASSEMBLY FOR USE WITH AN IMPLANTABLE MEDICAL DEVICE

(75) Inventors: Andrew J. Ries, Lino Lakes, MN (US); Jay K. Lahti, Shoreview, MN (US); George Patras, Greenfield, MN (US); John D. Longtin, Lake Elmo, MN (US); Bryan J. Zart, Shakopee, MN (US)

(73) Assignee: Medtronics, Inc., Minneapolis, MN (US)

( * ) Notice: Subject to any disclaimer, the term of this patent is extended or adjusted under 35 U.S.C. 154(b) by 0 days.

(21) Appl. No.: 12/171,337

(22) Filed: Jul. 11, 2008

(65) Prior Publication Data

US 2008/0268720 A1  Oct. 30, 2008

Related U.S. Application Data

(62) Division of application No. 11/281,008, filed on Nov. 17, 2005, now Pat. No. 7,413,482.

(51) Int. Cl.
*H01R 13/405* (2006.01)

(52) U.S. Cl. .............................. 439/736; 29/841; 607/36

(58) Field of Classification Search ................. 439/736, 439/884, 885, 909; 29/825, 841, 842; 607/36, 607/37
See application file for complete search history.

(56) References Cited

U.S. PATENT DOCUMENTS

| | | | |
|---|---|---|---|
| 5,235,742 A | 8/1993 | Szyszkowski | |
| 6,205,358 B1 | 3/2001 | Haeg et al. | |
| 6,817,905 B2 | 11/2004 | Zart et al. | |
| 2003/0040780 A1 | 2/2003 | Haeg et al. | |
| 2003/0082958 A1 | 5/2003 | Robinson et al. | |
| 2004/0093038 A1 | 5/2004 | Biggs et al. | |
| 2004/0116976 A1 | 6/2004 | Spadgenske | |
| 2005/0033138 A1 | 2/2005 | Ries et al. | |
| 2005/0137642 A1 | 6/2005 | Zart et al. | |

FOREIGN PATENT DOCUMENTS

| | | |
|---|---|---|
| EP | 1795226 | 6/2007 |
| WO | WO01/99239 | 12/2001 |
| WO | WO2005/112202 | 11/2005 |

*Primary Examiner*—Khiem Nguyen
(74) *Attorney, Agent, or Firm*—Stephen W. Bauer; Scott A. Bardell

(57) ABSTRACT

A sectional interconnect ribbon for use in a connector assembly for an implantable medical device is formed of two ore more separately-formed sections which are mechanically joined together to form an integral assembly. The sectional interconnect ribbon, as well as at least one connection element, is embedded within the connector assembly.

7 Claims, 5 Drawing Sheets

METHOD FOR FORMING A CONNECTOR ASSEMBLY FOR USE WITH AN IMPLANTABLE MEDICAL DEVICE

CROSS REFERENCE TO RELATED APPLICATIONS

This application is a divisional of U.S. Ser. No. 11/281,008, filed Nov. 17, 2005, now U.S. Pat. No. 7,413,482 now allowed, the disclosure of which is incorporated by reference in its entirety herein.

BACKGROUND OF THE INVENTION

Some of the embodiments of the present invention relate generally to the field of implantable medical devices, and more particularly, to a method for forming a connector assembly having a sectional interconnect ribbon embedded therein for use with an implantable medical device.

Implantable medical devices (IMDs) are becoming increasingly prevalent for the treatment of a wide variety of medical conditions. For example, cardiac pacemakers and implantable cardioverter-defibrillators have been developed for maintaining a desired heart rate during episodes of bradycardia and/or for applying cardioversion or defibrillation therapies to the heart upon detection of serious arrhythmias. In addition, tissue-stimulating IMDs are known for stimulating various nerves, muscles and organs to treat a variety of conditions.

Most IMDs include a hermetically-sealed housing that encloses a power source and electronic circuitry, at least one medical lead that bears at least one electrode and/or sensor, and a connector assembly (sometimes referred to as a header or block assembly) that electrically and mechanically couples the electronic circuitry in the housing to the electrodes and/or sensors via the medical leads. The specific electronic circuitry and lead configuration of the IMD depend upon the desired functionality of the IMD (i.e., whether it is a pacemaker, a nerve stimulator, or some other medical device).

Because the IMD housing is hermetically sealed, the medical leads preferably do not penetrate the housing, but rather are coupled to electrical connectors located within the connector assembly. To allow electrical signals to pass between the electronic circuitry of the IMD housing and the sensors and/or electrodes carried by the medical leads, the IMD housing is conventionally configured with feed-through conductors located on its outside surface yet electrically coupled to its internal circuitry. Once the connector assembly is physically attached to the IMD housing, the pass-through conductors are routed from the IMD housing to one of the conductors of the connector assembly. The pass-through conductors are then covered with a medical adhesive, and the adhesive is cured to form a protective, insulating layer that isolates the wires from external elements. Although this method is relatively straight forward, it requires manual routing of the conductors and application of the adhesive, which in turn introduces undesired variables into the manufacturing process.

An alternative approach to the use of adhesives involves the positioning of one or more conductors within a mold in a predetermined orientation. An insulating material is then injected into the mold to encapsulate the conductors. While this process eliminates the variables associated with a manual step, it is nevertheless difficult to implement with other than a simple design. This is because the introduction of the plastic into the mold at high pressures generally causes the position of the conductors to shift. Accordingly, in the molding process, shorts may form between conductors, or conversely, a desired electrical connection may be lost. While injection molding systems of this type generally include mechanisms to hold the conductors in place during the injection process, the components may shift regardless of efforts to prevent such shifting. Additionally, the difficulty associated with maintaining isolation between multiple conductors places limits on the assembly dimensions. That is, an assembly cannot be made too small because shorts are more likely to occur between closely spaced conductors that shift during the injection molding process. This may lead to a higher scrap rate than would otherwise exist.

U.S. Pat. No. 6,817,905 (which is hereby incorporated, in relevant parts, by reference) improves upon this method with the introduction of a two-shot method of forming a connector assembly. This method allows for the electrical conductors to be embedded within the connector assembly while reducing the likelihood of the electrical conductors shifting positions during the manufacturing process. According to this method, a core is formed of a first insulating material during a first injection molding step. The core is then loaded with various electrical connector elements. Next, the electrical conductors are secured to the core and are attached to a desired one of the electrical connector elements. In one embodiment, the electrical conductors are formed as a circuit assembly (i.e., an interconnect ribbon) that can be handled as a single unit during the assembly process. The circuit assembly may be stamped, or otherwise formed, from a single planar sheet of conductive material and then shaped for attachment to the core. In alternate embodiments, the electrical conductors are (1) individually loaded onto the core, (2) joined in a single circuit member via insulated material, or (3) integrally formed with the electrical connector elements.

In a second injection molding step, the electrical conductors (except for the electrical conductor pads), electrical connector elements, and the core are overmolded with a second insulating material. The electrical conductor pads are then separated, both electrically and mechanically, from each other.

BRIEF SUMMARY OF THE INVENTION

Some of the embodiments of the present invention relate to a sectional interconnect ribbon for use in a connector assembly for an implantable medical device. The sectional interconnect ribbon is formed of two or more separately-formed sections which are mechanically joined together to form an integral assembly. The sectional interconnect ribbon, as well as at least one connection element, is embedded within connector assembly.

During fabrication of the connector assembly, a core portion is formed on to which the at least one connection element is loaded. The sectional interconnect ribbon is then attached to the at least one connection element. Next, a structure is formed that extends over and adheres to at least a portion of the core element and to at least a portion of the sectional interconnect ribbon.

DETAILED DESCRIPTION

As will be described in greater detail below, the present invention primarily discloses embodiments relating to a sectional interconnect ribbon for use in a connector assembly for an implantable medical device (IMD). In designing a connector assembly, the number and configuration of both electrical connector elements and conductors may require an interconnect ribbon design that simply cannot be stamped, or otherwise formed, as a single unit from a planar sheet of conductive material. In these scenarios, the present invention provides a method and an apparatus for strategically dividing the interconnect ribbon into multiple interconnect ribbon pieces that can be assembled into a single unit to allow for a more efficient and less error-prone assembly process.

Figure 1:
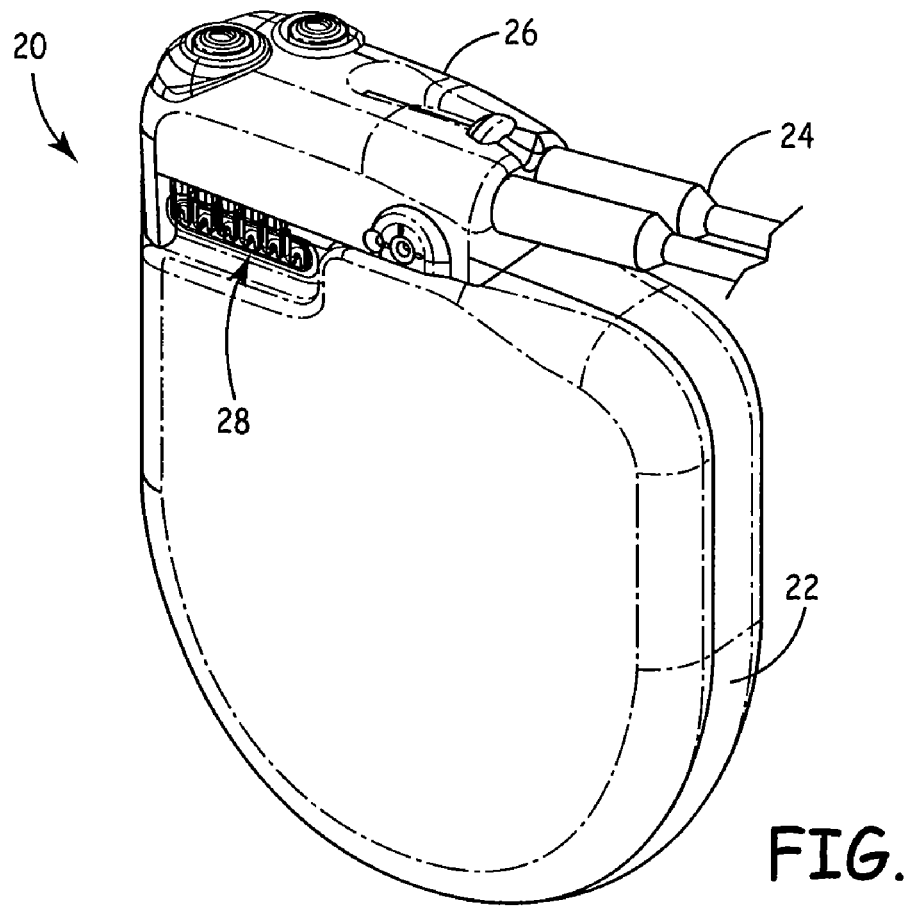
FIG. 1 is a perspective view of an implantable medical device having a connector assembly in accord with the present invention.

FIG. 1 is a perspective view of implantable medical device (IMD) 20 having housing 22, medical leads 24, and connector assembly 26. Implantable medical device 10 may be a cardiac pacemaker, cardioverter/defibrillator, a nerve stimulator, or any other type of medical device utilizing medical electrical leads 24. Housing 22 is a hermetically-sealed enclosure (or can) that houses a power supply and electronic circuitry. The function and composition of this electronic circuitry will vary depending upon the intended function of IMD 20. Housing 22 further includes pass-through connectors 28 to enable the electronic circuitry housed therein to communicate with medical leads 24 plugged into connector assembly 26 (sometimes referred to as a header or block assembly). Medical leads 24 typically include, for example, atrial and ventricular pacing/sensing leads and subcutaneous leads. Each lead may carry at least one electrode and/or sensor (not shown).

Figure 2:
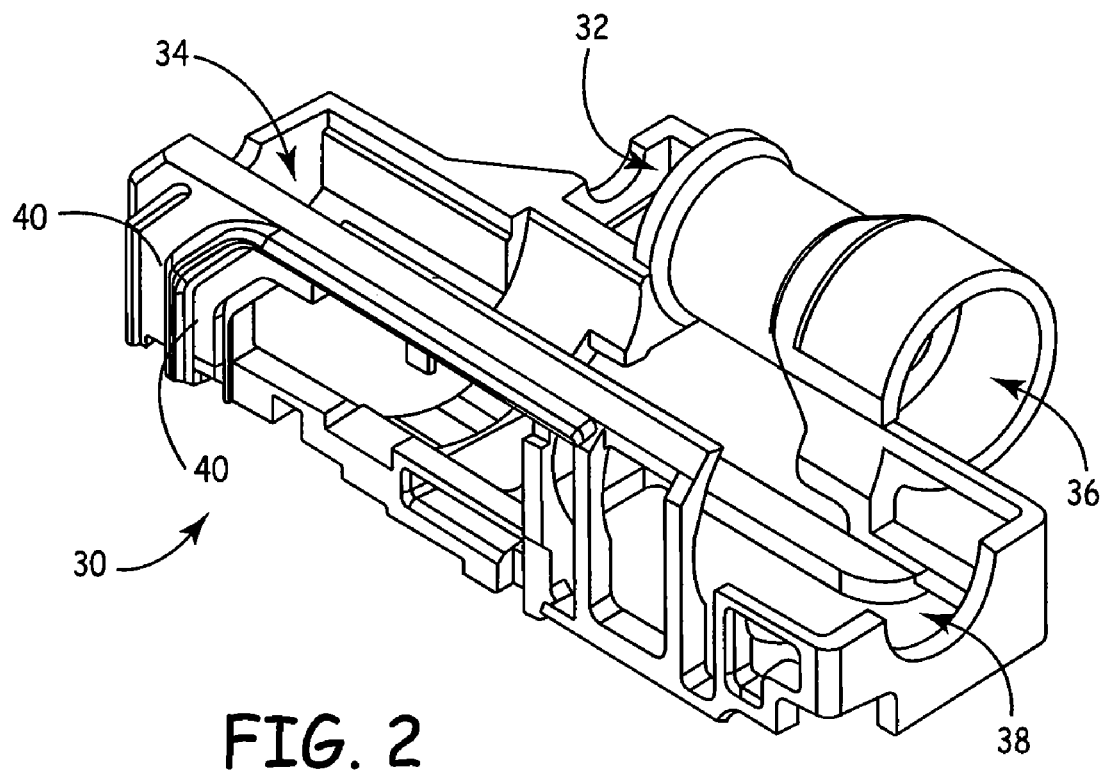
FIG. 2 is a perspective view of a core portion of the connector assembly.

FIG. 2 is a perspective view of core portion 30 of connector assembly 26. Core portion 30 is shaped to support various metal parts in a stable manner that can be maintained during an overmolding process to be discussed below. The specific shape of core portion 30, however, will be dictated by the number and types of conductive elements to be embedded in conductor assembly 26, the desired final shape of conductor assembly 26, and various other design considerations. For example, in the embodiment shown in FIG. 2, core portion 30 includes receptacles 32 and 34, each of which is adapted to receive a set-screw block, and receptacles 36 and 38, each of which is adapted to receive an electrical connector bore. Additionally, core portion 30 includes channels 40 along an external surface thereof for guiding the placement of electrical conductors.

Core portion 30 preferably is formed of a biocompatible thermoplastic material, such as, for example, without limitation, polyurethane. In one embodiment, core portion 30 is formed by heating the thermoplastic material to a temperature that is at, or slightly above, its melt point. The material is then injected into a primary mold and allowed to cool. After cooling, core portion 30 is removed from the mold. In an alternate embodiment, core portion 30 may be fabricated via a machining process.

Figure 3:
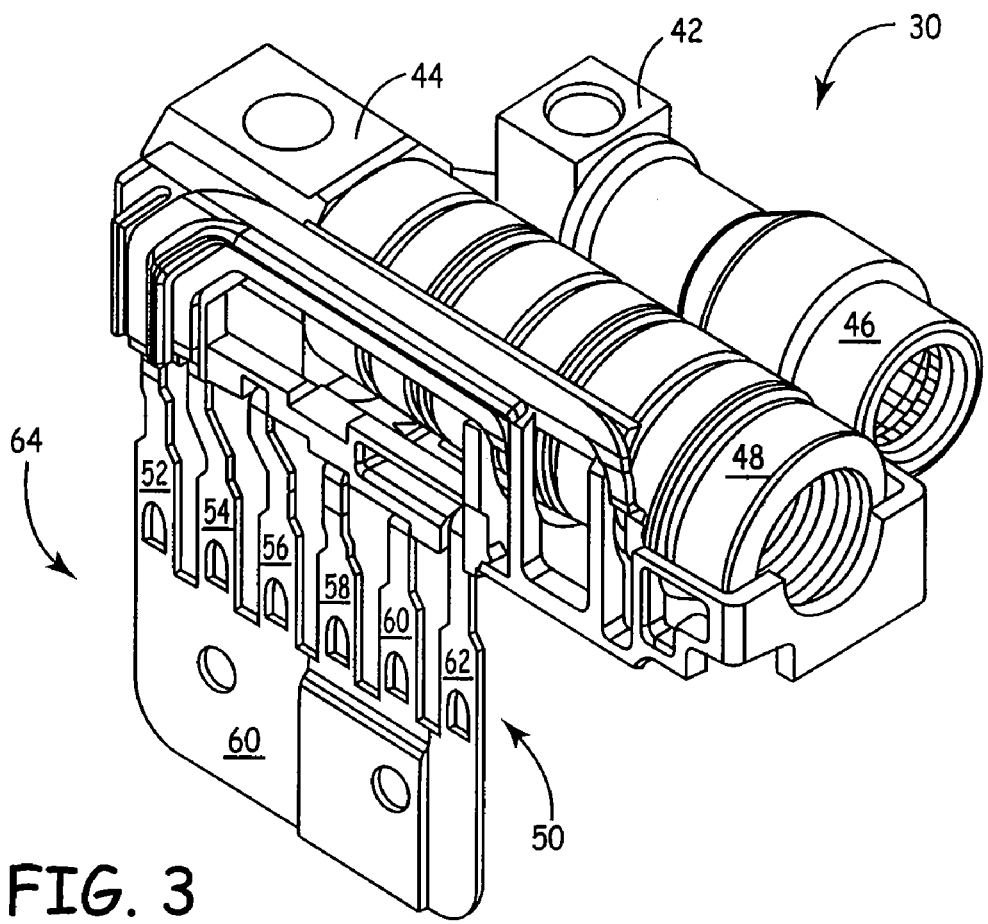
FIG. 3 is a perspective view of the core portion as loaded with various connector elements and a sectional interconnect ribbon in accord with the present invention.

FIG. 3 is a perspective view of core portion 30 of connector assembly 26 loaded with set-screw blocks 42 and 44, electrical connector bores 46 and 48, and sectional interconnect ribbon 50. At this stage of assembly, set-screw blocks 42 and 44 and electrical connector bores 46 and 48 are positioned loosely in receptacles 32, 34, 36, and 38, respectively. Set-screw blocks 42 and 44 and electrical connector bores 46 and 48 may be formed entirely, or partially of a conductive material, such as MP35N, stainless steel, or titanium. As is known in the art, set-screws 42 and 44 are used in conjunction with electrical connector bores 46 and 48 to electrically and mechanically couple to and secure in position proximal ends of medical leads 24. As shown in FIG. 3, electrical connector bore 46 conforms to an IS-1 standard for IMDs and electrical connector bore 48 conforms to an IS-4 standard. In alternate embodiments, the number and types of electrical connector elements may vary.

After core portion 30 has been loaded with these connector elements, sectional interconnect ribbon 50 is secured to the assembly. For example, sectional interconnect ribbon 50 is formed of a conductive material such as stainless steel, titanium, niobium, tantalum, or any other biocompatible conductive material. Interconnect ribbon 50 includes multiple traces or finger elements 52, 54, 56, 58, 60, and 62. At this stage of the assembly, finger elements 52-62 are mechanically and electrically joined together at tie bar portion 64 of sectional interconnect ribbon 50. This enables a more efficient and less error-prone assembly process because multiple elements need not be loaded individually onto core portion 30. Further, the likelihood of finger elements 52-62 shifting with respect to each other is reduced by having them formed in single interconnect ribbon 50.

Finger elements 52-62 of sectional interconnect ribbon 50 are adapted to be placed externally on a surface of core portion 30. As described above, core portion 30 includes channels 40 for guiding some of finger elements 52-62 into a desired position along the surface of core portion 30. In alternate embodiments, core portion 30 may include apertures through which some or all of finger elements 52-62 may be threaded.

Figure 4:
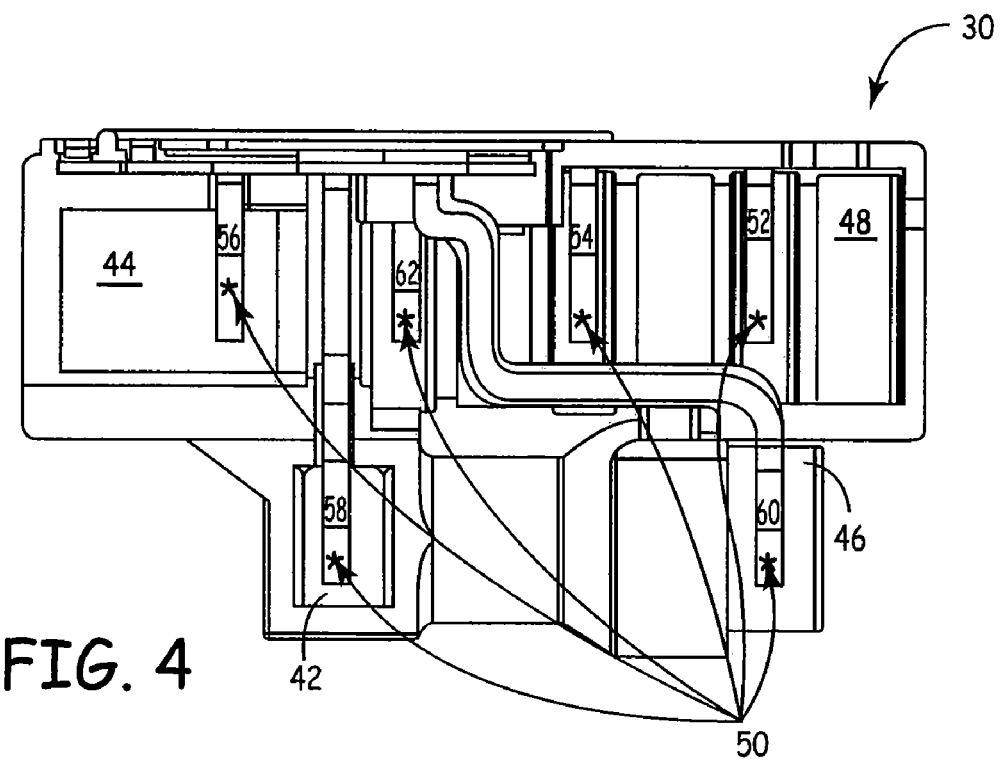
FIG. 4 is a bottom view of the loaded core portion illustrating electrical connections between the various connector elements and the sectional interconnect ribbon.

FIG. 4 is a bottom view of loaded core portion 30 illustrating electrical connections from sectional interconnect ribbon 50 to set-screw blocks 42 and 44 and electrical connector bores 46 and 48. In one manner of use, finger elements 52-62 are initially straight, and may be manually or automatically bent in the manner shown in FIGS. 3 and 4. In other embodiments, finger elements 52-62 are formed of a material that is deformable, and which may be temporarily straightened to be loaded onto core portion 30.

After sectional interconnect ribbon 50 is coupled to core portion 30, it may be soldered, welded, or otherwise attached to form predetermined electrical and mechanical connections between connector members and set-screw blocks and respective ones of the conductive finger elements. In the embodiment illustrated in FIG. 4, as denoted by asterisks, set-screw block 42 is welded to finger element 58; set-screw block 44 is welded to finger element 56; electrical connector bore 46 is welded to finger element 60; and electrical connector bore 48 is welded to finger elements 52, 54, and 62.

Figure 5:
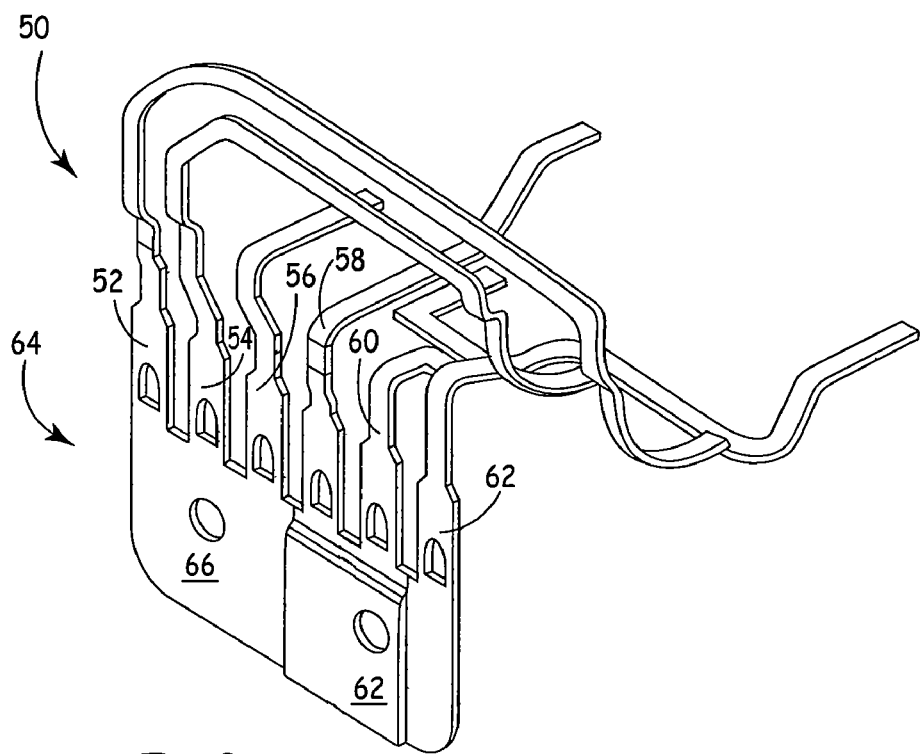
FIG. 5 is a perspective view of the sectional interconnect ribbon after it has been shaped to conform to the core portion.

FIG. 5 is a perspective view of sectional interconnect ribbon 50 as shaped to conform to core element 30. In this example, the arrangement of finger elements 52-62 is dictated by a specific configuration of set-screw blocks 42 and 44 and electrical connector bores 46 and 48, as well as the assigned electrical connections of each of finger elements 52-62 (as in turn dictated by the circuitry embedded within IMD housing 22).

Figure 6:
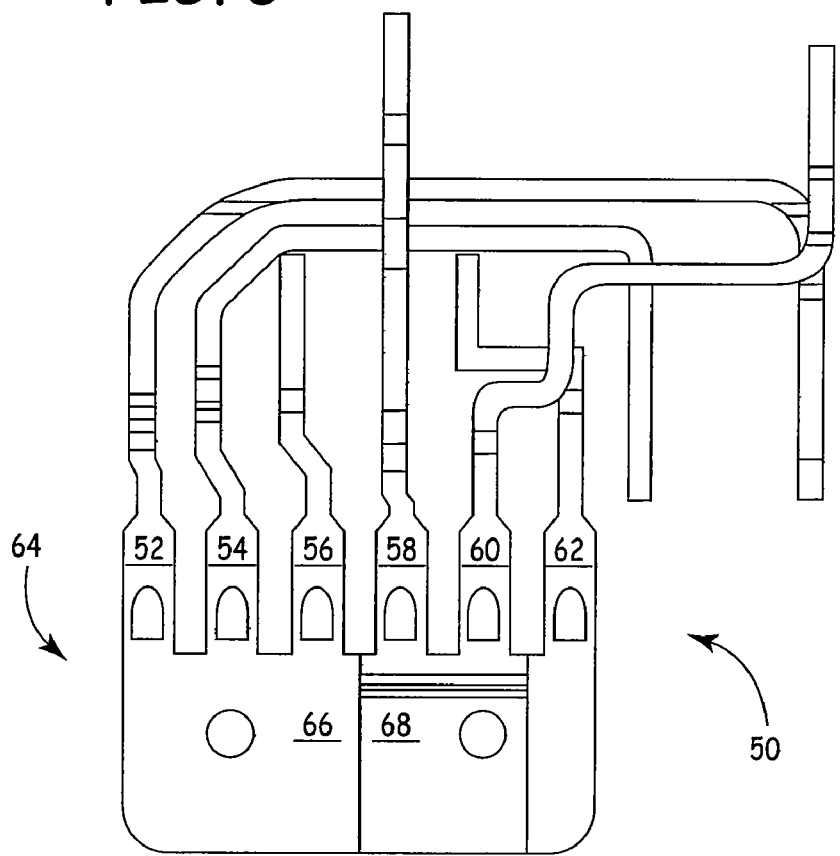
FIG. 6 illustrates the sectional interconnect ribbon prior to being shaped to conform to the core element.

FIG. 6 illustrates sectional interconnect ribbon 50 prior to being shaped to conform to core element 30. As is evident in this figure, interconnect ribbon 50 cannot be formed as a single unit from a planar sheet of conductive material because finger element 58 overlaps finger elements 52 and 54 and finger element 60 overlaps finger elements 52, 54, and 62. While it may have been possible to have reconfigured some of the connector elements and/or rearranged the assigned electrical connections of some of finger elements 52-62, this proposition would likely have significant redesign work. The present invention instead strategically divides interconnect ribbon 50 into first and second sections 66 and 68, each of which can be separately formed from planar sheets of conductive material and then subsequently assembled into a single unit. Thus, the present invention allows the technique of U.S. Pat. No. 6,819,905 to be used while accommodating designs that may be inconsistent with the interconnect ribbon being stamped from a single planar sheet. That is, the present invention gives the designer of the connector assembly greater freedom.

Figure 7:
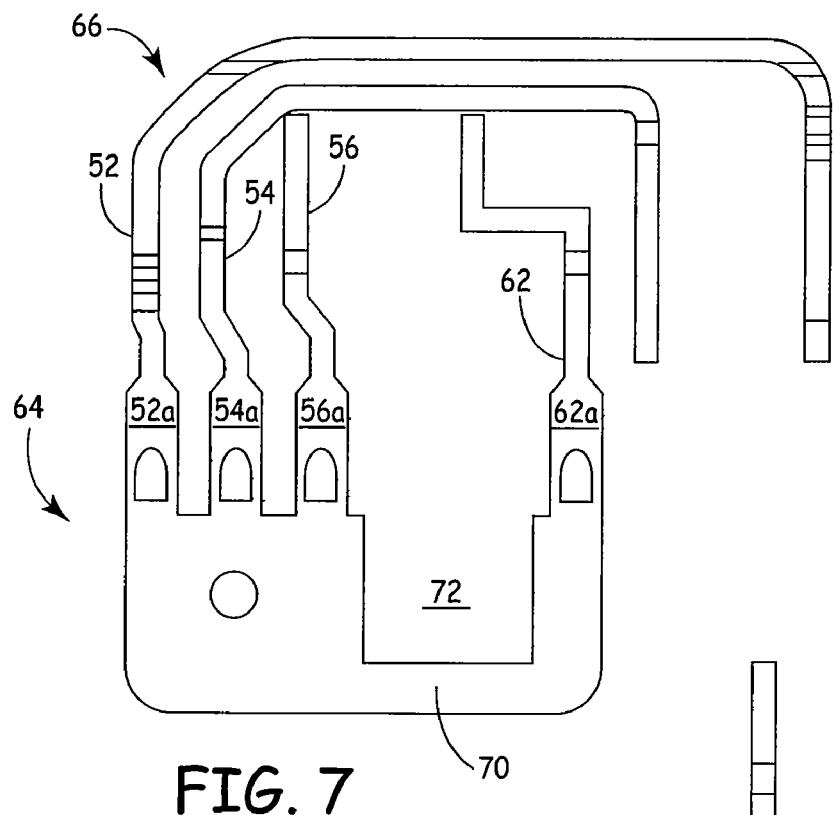
FIGS. 7-8 illustrate first and second sections, respectively, of the interconnect ribbon.
Figure 8:
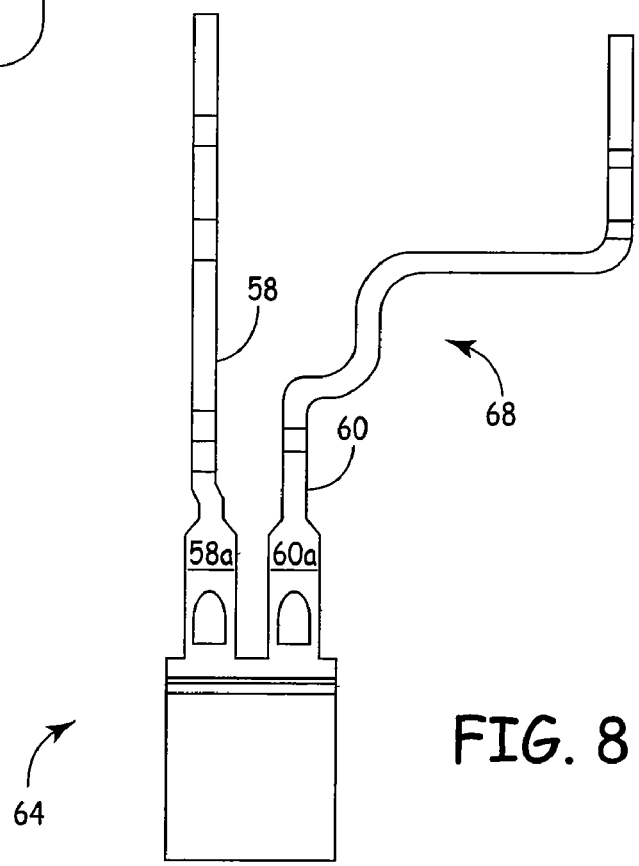

FIGS. 7 and 8 illustrate first and second sections 66 and 68, respectively, of the interconnect ribbon 50. Section 66 includes finger elements 52, 54, 56, and 62, while section 68 includes finger elements 58 and 60. Each of sections 66 and 68 is stamped from a planar sheet of conductive metal. Sections 66 and 68 are then assembled into a single unit for ease of handling. In particular, section 68 fits between finger elements 56 and 62 of section 66. In the embodiment illustrated in FIGS. 5-8, section 66 includes a sub-portion 70 of tie-bar portion 64 to which tie-bar portion 64 of section 68 is welded, soldered, or otherwise connected.

Each of finger elements 52-62 includes a connection pad 52a-62a intended for electrical and mechanical connection to pass-through connectors 58 of IMD housing 22. In this embodiment, each of connector pads 52a-62a resides in a single plane. Other embodiments, however, may demand a different configuration of its connector pads, as well as a different number and arrangement of finger elements. In the embodiment illustrated in FIGS. 5-8, tie-bar portion 64 of section 68 is bent to move connector pads 58a and 60a into the plane of connector pads 52a, 54a, 56a, and 62a.

The addition of this bend can be avoided in alternate embodiments by shaping tie-bar portion 64 of section 68 to fit in gap 72 of section 66. Sections 66 and 68 may then be joined by lap welds along the seams between sections 66 and 68 or by a supplemental tie-bar attached to tie-bar portions 64 of both sections 66 and 68.

Turning back to the manufacture of connector assembly 26, once all of the connector elements have been inserted into core portion 30 and sectional interconnect ribbon has been attached thereto, the resulting core assembly is then overmolded to form final connector 26. The process of preparing the core assembly for overmolding and the actual overmolding process are described in detail in U.S. Pat. No. 6,817,905, which is incorporated herein. In essence, however, this process involves the insertion of blocking elements into orifices of the connector elements to prevent the orifices from being filled with molding material; the insertion of loaded core portion 30 into a second mold cavity, the heating of a biocompatible thermoplastic material to a temperature that is at, or slightly above, its melt point; the injection of the heated thermoplastic material into the second mold; the cooling of the part; the ejection of newly-formed connector assembly 26 from the mold cavity, and the removal of tie-bar portion 64 of sectional interconnect ribbon 50 to separate finger elements 52-62 from each other.

Figure 9:
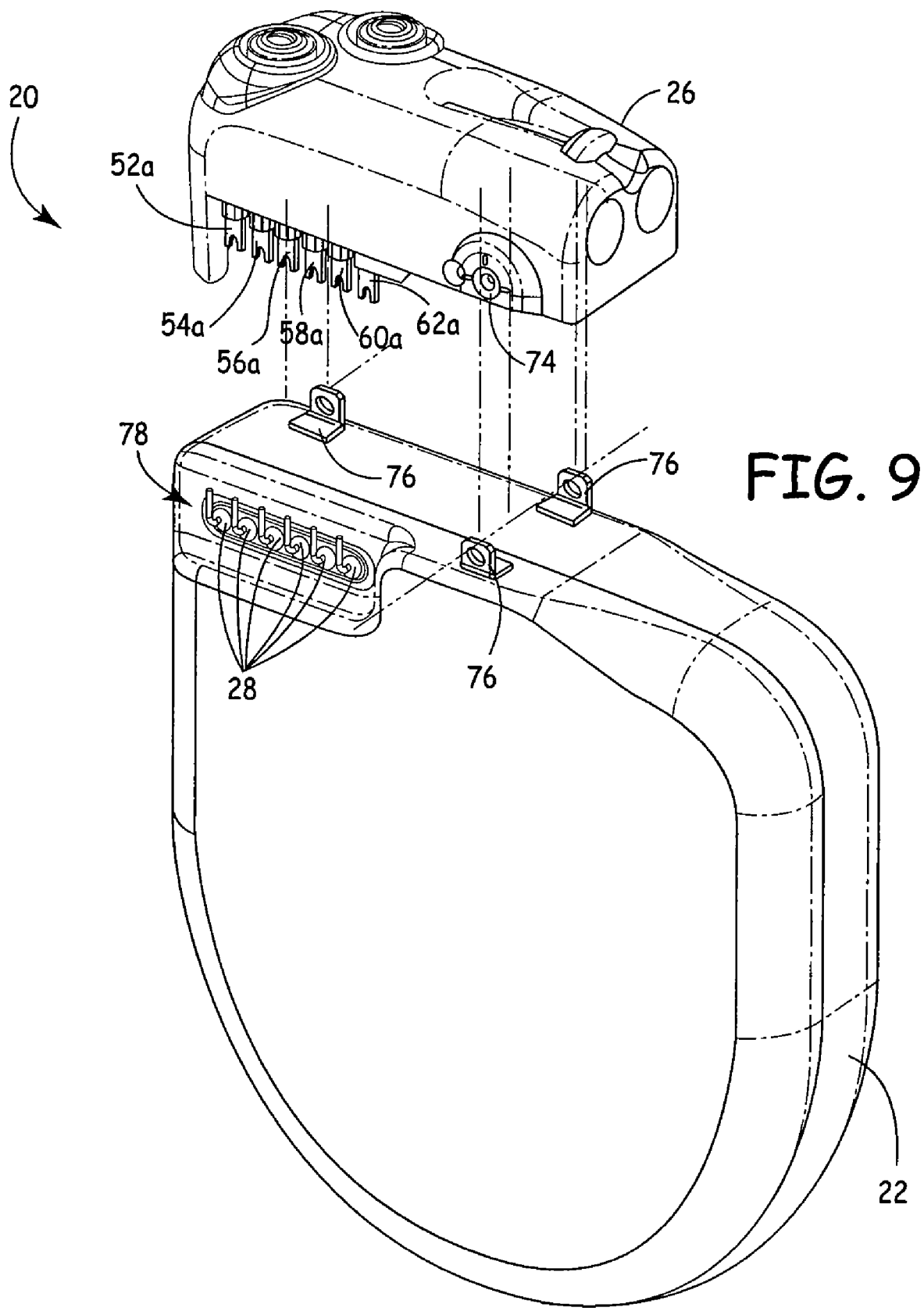
FIG. 9 is an exploded perspective view of the implantable medical device.

FIG. 9 is an exploded perspective view of IMD 20 illustrating the attachment of connector assembly 26 to housing 22. Connector assembly 26 and housing 22 include fastening elements 74 and 76, respectively, for affixing connector assembly 26 to housing 22. Connection pads 52a-62a of finger elements 52-62 each connect with a respective one of feedthrough pins 28 of housing 22. To ensure connectivity, connection pads 52a-62a are soldered, welded, or otherwise affixed to feedthrough pins 28. The area of these connections is then covered with a medical adhesive.

Although the present invention has been described with reference to preferred embodiments, workers skilled in the art will recognize that changes may be made in form and detail without departing from the spirit and scope of the invention. For example, while the present invention has been described above with reference to a two-step injection molding (or overmolding) process, the present invention is equally applicable to connection assemblies formed via (1) a two-shot casting process, (2) a two-shot injection molding process, (3) an injection molded first shot and a cast second shot process, and (4) a cast first shot and an injection molded second shot process. Additionally, the first shot, or the core portion, may be otherwise shaped or formed by a machining process.

The invention claimed is:

1. An interconnect ribbon assembly adapted for use in a connector assembly for an implantable medical device, the interconnect ribbon assembly comprising:
a first interconnect ribbon section comprising at least one conductive finger element and a tie-bar portion, each finger element having a free end for attachment to an electrical connector element of the connector assembly and a fixed end attached to the tie-bar portion;
a second interconnect ribbon section separately formed from the first interconnect ribbon section, the first interconnect ribbon section comprising at least one conductive finger element and a tie-bar portion, each finger element having a free end for attachment to an electrical connector element of the connector assembly and a fixed end attached to the tie-bar portion; and
a mechanical joint mechanically joining the tie-bar portions of the first and second interconnect ribbon sections.

2. The interconnect ribbon assembly of claim 1, wherein at least one of the conductive finger elements of the first interconnect ribbon section when laid flat overlaps at least one of the conductive finger elements of the second interconnect ribbon section when laid flat.

3. The interconnect ribbon assembly of claim 1, wherein the fixed ends of the first and second interconnect ribbon sections have generally planar profiles that reside in substantially the same plane.

4. The interconnect ribbon assembly of claim 1, wherein the tie-bar portions of the first and second interconnect ribbon sections are mechanically joined together via a lap weld joint.

5. The interconnect ribbon assembly of claim 1, wherein the tie-bar portions of the first and second interconnect ribbon sections are mechanically joined together via a supplemental tie-bar attached to the tie-bar portions of the first and second interconnect ribbon sections.

6. The interconnect ribbon assembly of claim 1, wherein the first and second interconnect ribbon sections are each formed from a generally planar sheet of conductive material.

7. The interconnect ribbon assembly of claim 1, wherein the first and second interconnect ribbon sections are each formed of a material selected from a group consisting of stainless steel, titanium, niobium, tantalum, and combinations thereof.

* * * * *

UNITED STATES PATENT AND TRADEMARK OFFICE
CERTIFICATE OF CORRECTION

PATENT NO. : 7,537,493 B2 Page 1 of 1
APPLICATION NO. : 12/171337
DATED : May 26, 2009
INVENTOR(S) : Ries et al.

It is certified that error appears in the above-identified patent and that said Letters Patent is hereby corrected as shown below:

(73) On first page cover, under Assignee, delete "Medtronics" and insert in place thereof, --Medtronic--; and

(57) On first page cover, under Abstract, delete "two ore more" and insert in place thereof --two or more--.

Signed and Sealed this

Fourth Day of August, 2009

JOHN DOLL
*Acting Director of the United States Patent and Trademark Office*